(12) United States Patent
Kane et al.

(10) Patent No.: US 7,998,925 B2
(45) Date of Patent: Aug. 16, 2011

(54) SPATIALLY-DEFINED MODIFICATION OF FRESH TISSUE USING COVALENT CHEMISTRY

(75) Inventors: Robert R. Kane, Waco, TX (US); Aruna Perera, Waco, TX (US)

(73) Assignee: Baylor University, Waco, TX (US)

( * ) Notice: Subject to any disclaimer, the term of this patent is extended or adjusted under 35 U.S.C. 154(b) by 0 days.

(21) Appl. No.: 11/237,000

(22) Filed: Sep. 28, 2005

(65) Prior Publication Data
US 2006/0177923 A1    Aug. 10, 2006

Related U.S. Application Data (60) Provisional application No. 60/613,827, filed on Sep. 28, 2004.

(51) Int. Cl.
*C07K 14/00* (2006.01)
*A61K 31/00* (2006.01)

(52) U.S. Cl. .......................................... 514/2; 424/78.17

(58) Field of Classification Search ........................ None
See application file for complete search history.

(56) References Cited

U.S. PATENT DOCUMENTS

| 5,821,343 | A | * | 10/1998 | Keogh | ........................... | 530/402 |
| 5,977,252 | A | | 11/1999 | Wagner et al. | | |
| 6,570,040 | B2 | | 5/2003 | Saxon et al. | | |
| 6,861,211 | B2 | * | 3/2005 | Levy et al. | ...................... | 435/1.1 |

FOREIGN PATENT DOCUMENTS

| EP | 0 732 110 A1 | 9/1996 |
| WO | WO 02/00685 A1 | 1/2002 |

OTHER PUBLICATIONS

Bank et al., Surface engineering of living myoblasts via selective periodate oxidation, Mar. 30, 2003, vol. 81, No. 7, pp. 800-808.*
McFetridge et al. "Preparation of porcine carotid arteries for vascular tissue engineering applications", Journal of Biomedical Materials Research Part A, vol. 70A, Issue 2, pp. 224-234 (Jun. 2004).*
Hermanson, G. Bioconjugate Techniques, Academic Press, pp. 19-21, and 114-116 (1996).*
De La Fuente EK, Dawson CA, Nelin LD, Bongard RD, McAuliffe TL, Merker MP. Biotinylation of membrane proteins accessible via the pulmonary circulation in normal and hyperoxic rats. Am J Physiol. Mar. 1997;272(3 Pt 1):L461-70.
Halfter W. Anterograde tracing of retinal axons in the avian embryo with low molecular weight derivatives of biotin. Dev Biol. Feb. 1987;119(2):322-35.
Hoya K, Guterman LR, Miskolczi L, Hopkins LN. A novel intravascular drug delivery method using endothelial biotinylation and avidin-biotln binding. Drug Deliv. Oct.-Dec. 2001;8(4):215-22.
Hoffman-Fezer G, Maschke H, Zeitler HJ, Gais P, Heger W, Ellwart J, Thierfelder S. Direct in vivo biotinylation of erythrocytes as an assay for red cell survival studies. Ann Hematol. Oct. 1991;63(4):214-7.
Partial International Search from the PCT dated Mar. 16, 2006.
Bank De P A et al: "Surface engineering of living myoblasts via selective periodate oxidation" Biotechnology and Bioengineering—Combinatorial Chemistry, Wiley, New York, NY, US, vol. 81, No. 7, Mar. 30, 2003, pp. 800-808.
Fabris F et al: "Labeling of Platelet Surface Glycoproteins With Biotin Derivatives" Thrombosis Research, Tarrytown, NY, US, vol. 66, No. 4, May 15, 1992, pp. 409-419.
Bayer E A et al: "Biocytin Hydrazide—A Selective Label for Sialic Acids, Galactose,and Other Sugars in Glycoconjugates Using Avidin-Biotin Technology" Analytical Biochemistry, Academic Press, New York, NY, US, vol. 170, No. 2, 1988, pp. 271-281.
Rando R R et al: "Labeling of Oxidized Cell Surface Membranes by Acyl Hydrazides" Biochimica et Biophysica Acta, vol. 557, No. 2, 1979, pp. 354-362.
Huestis W H: "Preliminary characterization of the acetylcholine receptor in human erythrocytes" Journal of Supramolecular and Cellular Biochemistry 1976, vol. 4, No. 3, 1976, pp. 355-365.
Karlin A et al: "The affinity labeling of partially purified acetylcholine receptor from electric tissue of Electrophorus" Proceedings of the National Academy of Sciences of the United States of America 1973, vol. 70, No. 12, 1973, p. 1.
Burns J A et al: "Selective reduction of disulfides by tris(2-carboxyethyl)phosphine" Journal of Organic Chemistry, American Chemical Society. Easton, US, vol. 56, No. 8, 1991, pp. 2648-2650.
European Patent Office, International Preliminary Report on Patentability, Application No. PCT/US2005/034991, Apr. 3, 2007.
European Patent Office, International Search Report, Application No. PCT/US2005/034991, Mar. 9, 2007.
European Patent Office, Communication Pursuant to Article 94(3) EPC, Application No. PCT/US2005/034991, Dec. 7, 2010.

* cited by examiner

*Primary Examiner* — Anand Desai
(74) *Attorney, Agent, or Firm* — Jackson Walker L.L.P.

(57) ABSTRACT

Methods for modification of tissue using covalent chemistry. Tissue can be modified through direct alkylation, reduction followed by alkylation, or oxidation followed by condensation to covalently attach small organic molecules or appropriately modified proteins. The modification can be spatially limited to desired regions of the tissue surface.

6 Claims, 10 Drawing Sheets

Carboxylic acid active ester

Sulfonic acid active ester

Phosphonic acid active ester

3 Biotin-Hydrazide

4 Biotin-Maleimide

SPATIALLY-DEFINED MODIFICATION OF FRESH TISSUE USING COVALENT CHEMISTRY

This application claims priority to U.S. Provisional Patent Application, Ser. No. 60/613,827, entitled "Spatially-Defined Modification of Fresh Tissue Using Covalent Chemistry" filed on Sep. 28, 2004, the entire content of which is hereby incorporated by reference.

BACKGROUND

This invention relates to a method for the covalent modification of tissue with small molecules and functional proteins.

The importance of interactions between proliferating cells and substrate surfaces, and especially surface proteins and carbohydrates, has long been an active area of study. It is increasingly well understood how surface molecular composition, topology, and geometric patterning of extracellular matrix ("ECM") molecules influence specific biological processes and have a critical role in cell growth regulation and differentiation, cell migration, apoptosis, and general morphogenesis. Accordingly, there has been significant effort expended to develop methods to create surfaces for tissue culture that are patterned with specific biologically relevant molecules in order in influence the aforementioned properties.

A variety of methods are known for the chemoselective modification of specific functional groups found in complex proteins. In general, this chemistry is solution chemistry, and these methods have been developed for the modification of soluble proteins. The electrophilic aromatic substitution of the tyrosine phenol functionality is a very specific example. Often, chloramine-T is used to reduce iodide, resulting in the introduction of iodine (most often a radioactive isotope such as I-129 or I-131) into the protein's tyrosine residues at the position ortho to the phenol. However, this chemistry is limited, as the conjugation of complex molecules to the target protein is often the goal.

For a more general example, the amine residues found in most proteins (at the N-terminus as well as from lysine residues) are readily modified, most commonly with electrophilic acylating agents. While this chemical modification is straightforward and relatively general, there are often numerous amines that exhibit similar reactivity in a given protein, and this methodology is considered to be rather non-selective. Additionally, this strategy precludes the use of amine-containing functionalities in the acylating agent, therefore dramatically limiting the structural complexity of the modification reagent.

A functional group that has proven extremely useful for site-specific protein modification is the free sulfhydryl. This functionality can be either found in native protein (for example in albumin), revealed via the reduction of disulfides bonds found in the native protein (for example, the reduction of F(ab)2 IgG antibody fragments to release Fab-SH fragments), or introduced into the protein by reaction with a reagent such as Traut's reagent. Protein-bound thiol groups can be selectively alkylated using maleimide reagents or α-halo carbonyl compounds (although this is typically less chemoselective, as α-halocarbonyls also react with protein amines at a competitive rate). Since free sulfhydryls are rarely found in native protein, the number of reducible disulfides is usually very limited, and the maleimide alkylation of thiols is very chemoselective, this chemistry is considered to be more precise and controllable than the amine alkylation methodology. Additionally, the chemoselectivity of this methodology allows the use of highly functionalized conjugation reagents.

Many additional methods for the modification of soluble proteins have been developed but have been applied much less widely. For example, carbonyl residues generated by the oxidation of sugar residues found in glycosylated proteins can be reacted with amines (reductive alkylation) or hydrazide-containing reagents (to afford hydrazones). However, at this time there have been no reports of producing patterns of functional proteins on fresh tissue surfaces.

SUMMARY

This invention relates to methods for modifying tissue using covalent chemistry.

A variety of collageneous tissues can be readily modified, including bovine meniscus, aorta, pericardium, and cornea, as well as fetal pig skin. These tissues can be either modified in a spatially defined manner (by physically limiting the sites of exposure of the tissue to the reagents), or in a uniform, bulk fashion (by exposing the entire tissue sample to the desired reagents).

The tissue modification can be performed on "unactivated" surfaces by using amine-reactive reagents (electrophilic reagents such as active esters). Alternatively, the tissue surface can first be activated to generate reactive species in addition to those found in the native tissue. For example, tissue disulfides can be selectively reduced by the phosphine reductant triscarboxyethylphosphine. Subsequently, the reduced tissue surface will react with a thiol-reactive electrophile such as a maleimide. A second activation strategy is periodate-based oxidation, which results in the conversion of geminal diols, such as those found in the proteoglytcan tissue matrix, to carbonyl compounds. This oxidation can be followed with reaction of the tissue surface with nucleophilic reagents such as hydrazides.

The tissue surface covalent modification step may involve a condensation reaction with either a small organic molecule (such as biotin hydrazide or the N-hydroxysuccinimide ester of biotin) or an appropriately-modified protein (such as maleimide-substituted avidin). Whichever strategy is used, the modifications are functional. The tissue-bound biotin retains its ability to bind to avidin, and the tissue-bound avidin is able to bind biotin-substituted molecules (including biotinylated proteins).

The presence of the desired tissue surface modifications has been primarily detected using chemiluminescent techniques. For biotin-modified surfaces, avidin-horseradish peroxidase can be selectively immobilized and will provide a signal (light) in the presence of luminal. Similarily, biotinylated horseradish peroxidase can be used in the detection of avidin-modified tissues.

A number of practical applications can be proposed for a technology that allows patterns of proteins on fresh tissue surfaces. These include enhancing or reducing specific protein and cellular adhesions (useful in transplantation and the use of autologous, engineered, or foreign tissue in therapy), directing morphogenesis for the development of specific cell types in specific locations, and the recruitment of immune or healing responses.

One application is in the area of wound healing. By attaching proteins or other molecules directly to the site of injury a localized healing effect can be stimulated. For example, the immobilization of soluble tissue factor to wound surfaces should result in local thrombosis and the accompanying release of soluble proteins that enhance healing. Other proteins involved in wound healing could also be used. Alternatively, anti-coagulant proteins or peptides such as a tissue factor pathway inhibitory peptide could be used to avoid clotting at certain defined sites, again potentially enhancing wound care. Proteins or peptides could be incorporated after angioplasty to slow cell growth and avoid restenosis.

This methodology could also be used in tissue engineering. For example, angiogenesis could be enhanced in a spatially designed fashion in artificial organs by the use of well characterized angiogenic proteins and peptides. As a specific example, cultured skin could be modified in a spatially defined fashion with proteins aimed at enhancing cell adhesion or the development of a capillary network (angiogenesis).

As a final example, tissue immunogenicity could be enhanced by modifying surfaces with immunogenic protein or peptides. This could be used to potentially elicit an immune response to a given tissue—for example a solid tumor that has escaped the immune system.

DETAILED DESCRIPTION OF PREFERRED EMBODIMENTS

There are several schemes and methods which can be utilized for modification of tissue using covalent chemistry. The modifying agent can be a protein or a small compound such as biotin. Depending on the scheme used for modification, the modifying agent can have an active ester functionality, a hydrazide functionality, or a maleimide functionality.

Figure 1:
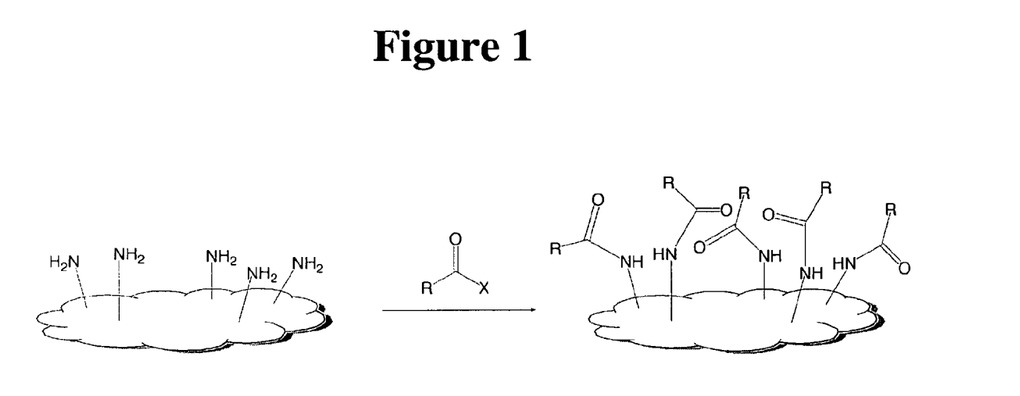
FIG. 1 shows a general scheme for direct alkylation of tissue surface amines.
Figure 2:
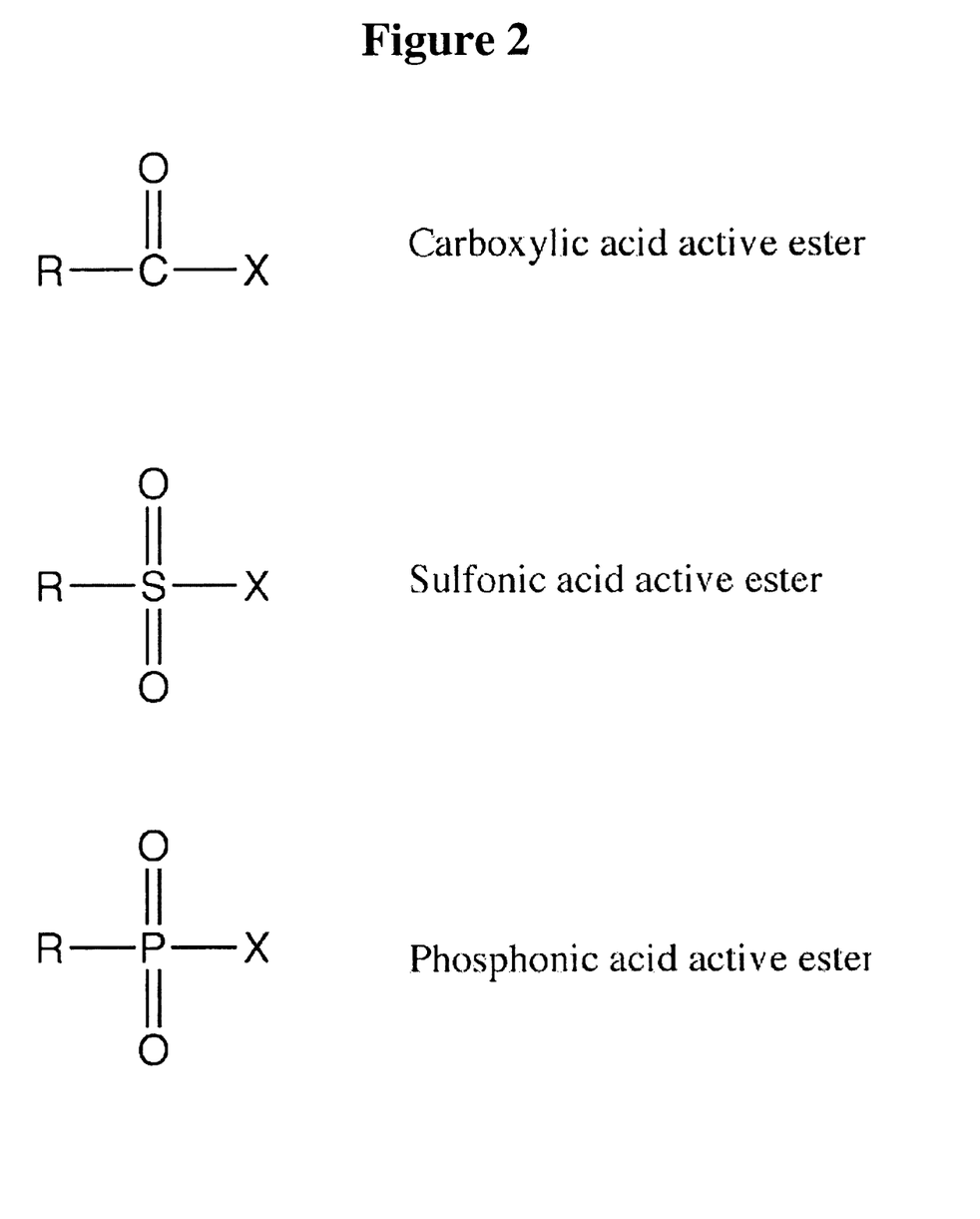
FIG. 2 shows general examples of active ester functionalities.

In a first general scheme, the tissue can be modified by direct alkylation. Unactivated tissue surfaces can be covalently modified by a variety of active esters, as shown in the general scheme illustrated in FIG. 1. Groups on the tissue surface which will be alkylated by the active ester functionality include any amine groups, especially lysine epsilon amino groups and the N-terminus of proteins. Any modifying agent with an active ester functionality or group can be used for the alkylation. Agents with active ester groups include those with leaving groups. General structures for active ester functionalities are shown in FIG. 2. In the structures shown in FIG. 2, the group "X" is the leaving group. A leaving group is generally defined as that part of a substrate molecule which is cleaved in a heterolytic reaction and which usually doesn't contain carbon. Some preferred examples of the leaving group "X" include halogens, especially bromine, chlorine, and fluorine, tetrafluorophenoxy, pentafluorophenoxy, azido, N-hydroxysuccinimido ("NHS"), 2-sulfo-NHS, anhydride (carboxylate, sulfonate, or phosphonate), alkyl thiolate, and aryl thiolate.

Figure 3:
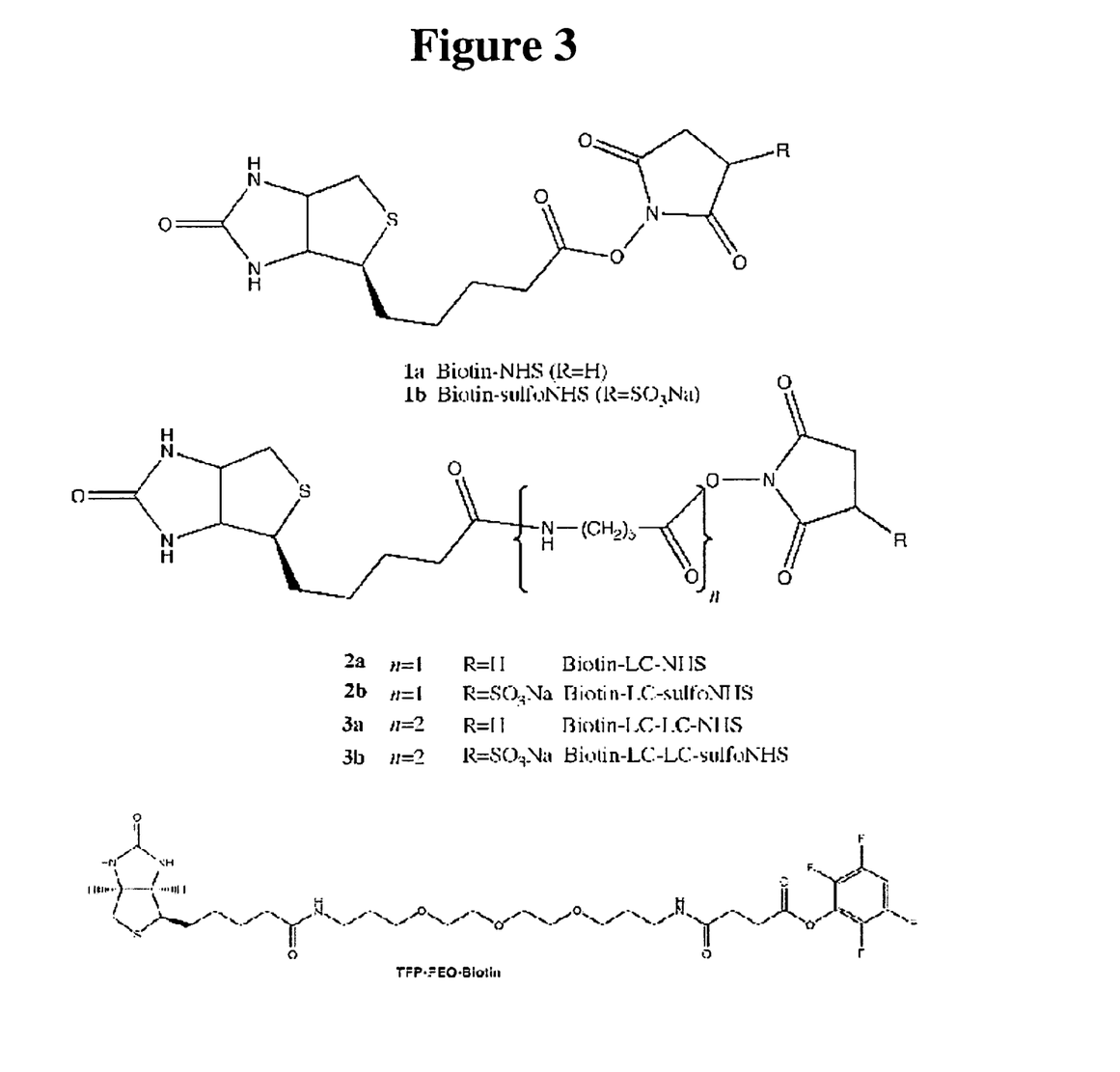
FIG. 3 shows examples of biotin active esters which can be used for direct tissue alkylation.

In a preferred embodiment, biotin derivatives such as biotin active esters can be covalently attached to tissue surface amines through direct alkylation. Examples of preferred biotin derivatives include biotin-NHS, biotin-sulfoNHS, biotin-LC-NHS, biotin-LC-sulfoNHS, biotin-LC-LC-NHS, and biotin-LC-LC-sulfoNHS which are illustrated in FIG. 3. "LC" stands for "long chain," which represents a seven atom spacer between biotin and the NHS ester. Another example of a preferred biotin derivative is tetrafluorophenyl polyethylene oxide biotin (TFP-PEO-biotin), which is also shown in FIG. 3. The active ester reagents are preferably used at about 0.05-0.5 M concentrations, and more preferably at 0.1 M concentrations, in phosphate buffered saline ("PBS") or in a solution of 9:1 PBS to dimethylsulfoxide ("DMSO"), if necessary for solubilization. The active ester compounds are preferably incubated with the tissue at room temperature for about 12 hours. The direct alkylation modification can be carried out at spatially-defined regions on the tissue surface by physically restricting the area of tissue surface which comes into contact with the biotin active ester.

In a second general scheme, the tissue can be modified by oxidation of the tissue surface followed by condensation with hydrazide reagent to form a hydrazone linkage. This is shown in the general scheme illustrated in FIG. 4. Any modifying agent having a hydrazide functionality can be used in the condensation step. This method for tissue modification involves the exposure of the desired regions of the tissue surface to a PBS solution of sodium periodate, preferably at about 0.05-0.5 M, and more preferably at 0.08 M, for about 4-8 hours at room temperature. The oxidized tissue surface can then be covalently modified by exposure to modifying agents such as hydraze derivatives. A condensation reaction with the hydraze derivative forms a hydrazone linkage. A preferred example of a hydrazide reagent is biotin hydrazide, which is illustrated as Compound 3 in FIG. 5. A solution of biotin hydrazide in PBS:DMSO (9:1), preferably at about 10-100 µM, and more preferably at 12 µM, is then exposed to the tissue surface. The exposure is preferably for about 10-15 hours at 4° C.

Figure 6:
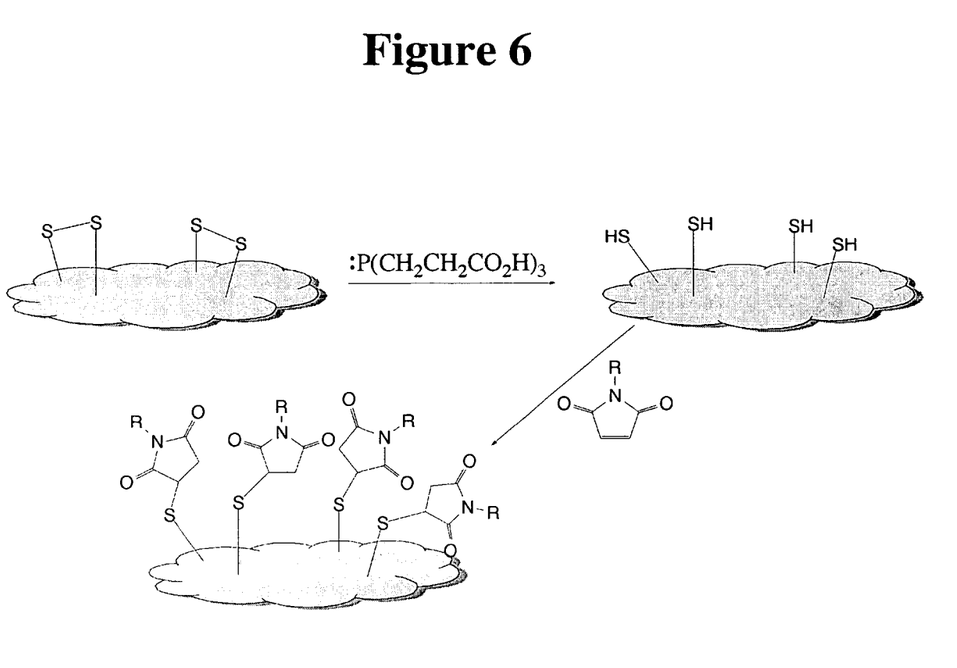
FIG. 6 shows a general scheme for reduction of the tissue surface, followed by maleimide-based alkylation.
Figure 7:
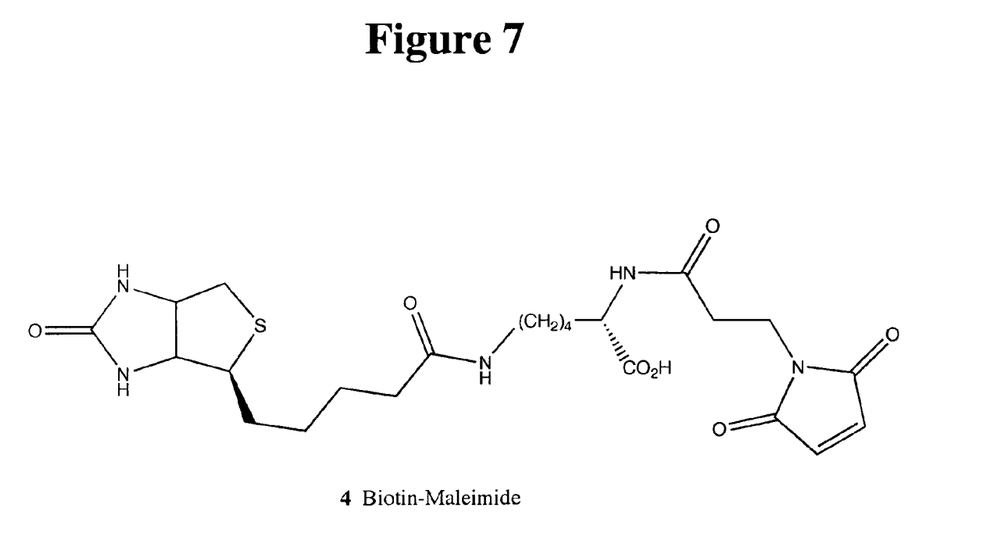
FIG. 7 shown an example of a biotin maleimide reagent.

A third example of a method for tissue modification involves reduction of the tissue surface followed by alkylation. The general scheme for reduction followed by alkylation is shown in FIG. 6. Any modifying agent having a maleimide functionality can be used in the alkylation step. Reductive activation involves exposure of the tissue surface to a PBS solution of triscarboxyethylphosphine ("TCEP"), preferably at about 0.05-0.5 M and more preferably at 0.1 M, for a short period of time, or about 1-30 minutes, at room temperature. The reduced tissue surface can then be modified by exposure to electrophilic reagents such as maleimides or ox-halo carbonyl compounds. Preferably, biotin maleimide, which is illustrated as Compound 4 in FIG. 7, can be used to modify reductively activated tissue surfaces. The biotin maleimide, preferably at about 0.01-0.1 M, and more preferably at 0.05 M, in 9:1 PBS:DMSO, is exposed to the activated tissue preferably at room temperature for about 1-4 hours. Alternatively, functionalized proteins such as avidin-maleimide, preferably at about 0.1 to 1 mg/ml in PBS, and more preferably at 0.25 mg/ml, and horseradish peroxidase-maleimide can directly alkylate free thiols on reductively-activated tissue surfaces. In one preferred example, exposure of a reductively activated tissue surface to a 0.20 mg/ml solution of avidin-maleimide in PBS for about 1-4 hours at room temperature results in the covalent immobilization of functionally-competent avidin protein.

Figure 4:
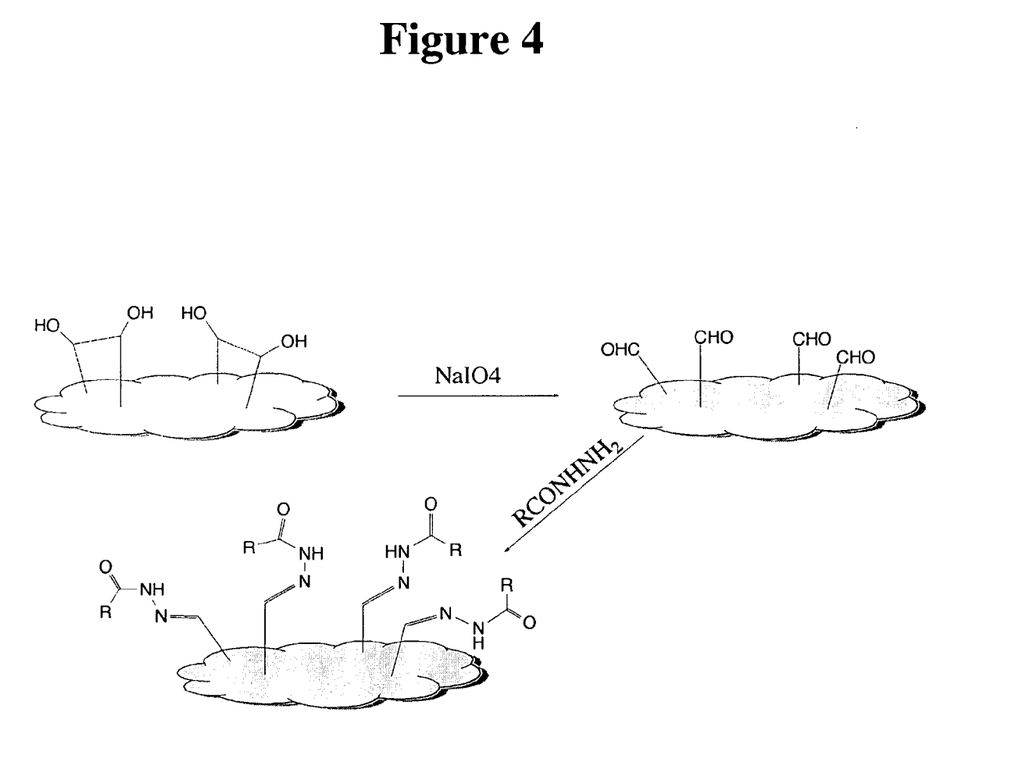
FIG. 4 shows a general scheme for oxidation of the tissue surface, followed by condensation with a hydrazide reagent to form a hydrazone linkage.
Figure 5:
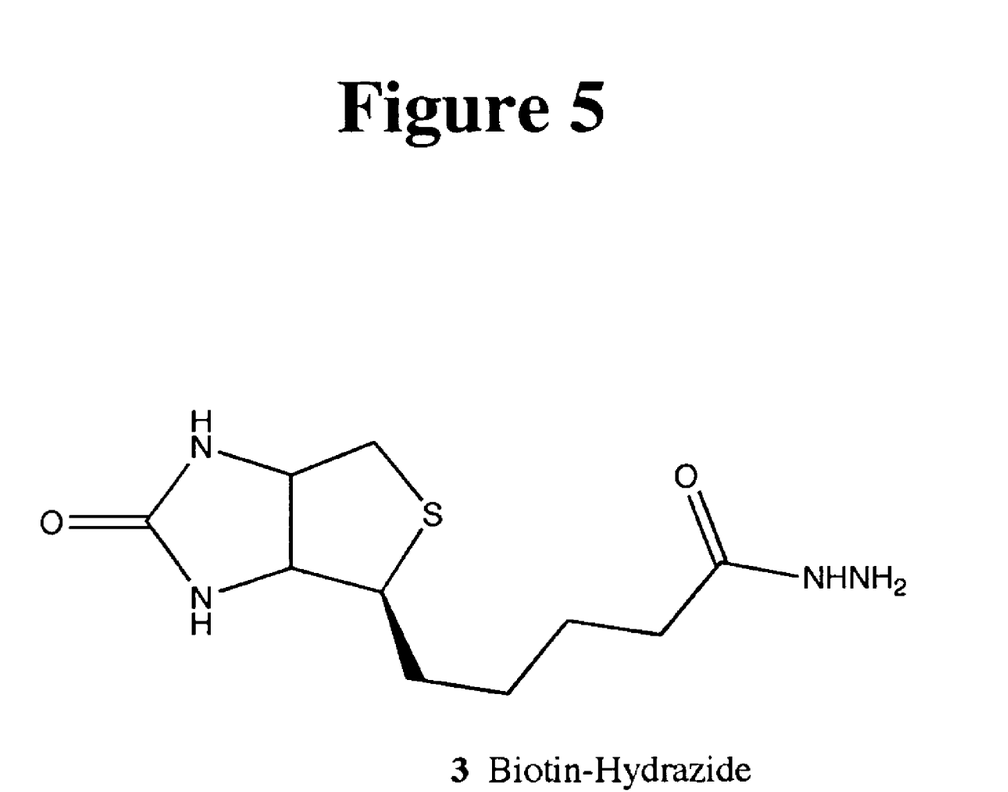
FIG. 5 shows an example of a biotin hydrazide reagent.

The most common and preferred method for detecting the tissue modification is chemiluminescence. If the modifying reagent, which is illustrated as "R" in FIGS. 1, 4, and 6, is inherently fluorescent it could be detected by measuring its fluorescence directly. Unfortunately, the background tissue fluorescence can make this difficult. The preferred device for detection of the chemiluminescence of the tissue modification is the Bio-Rad Fluor-S Multi-Imager (Bio-Rad Laboratories, Inc., Hercules, Calif.).

Figure 8:
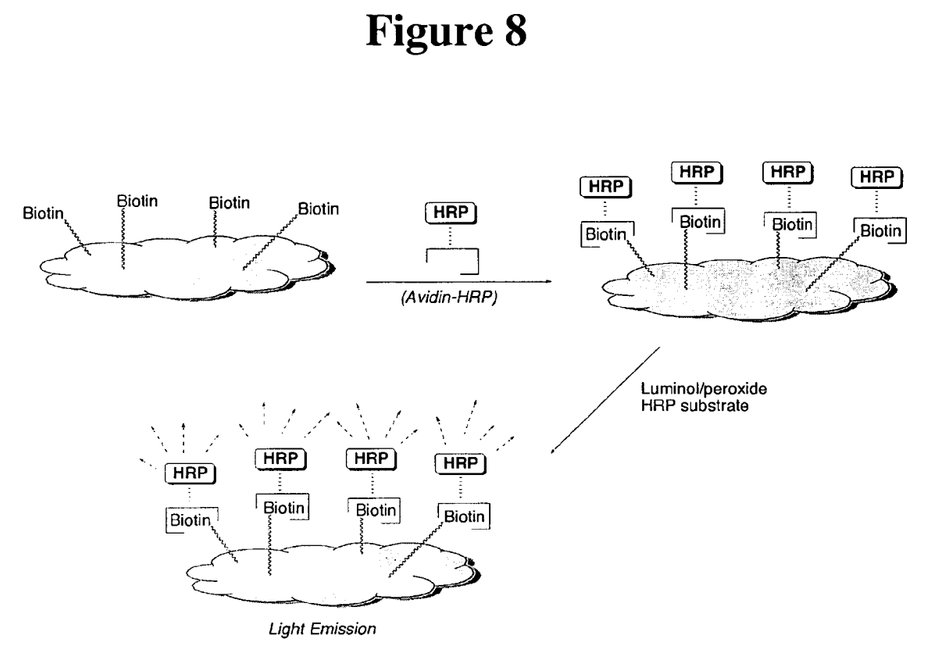
FIG. 8 shows a general scheme for detection of biotin-modified tissue by chemiluminescence.

Biotinylated tissue surfaces can be readily detected using a chemiluminescent assay based on the selective binding of avidin-horseradish peroxidase (avidin-HRP) and the subsequent emission of light after exposure of the avidin-HRP to an appropriate substrate. A general scheme for this detection method is shown in FIG. 8.

Figure 9:
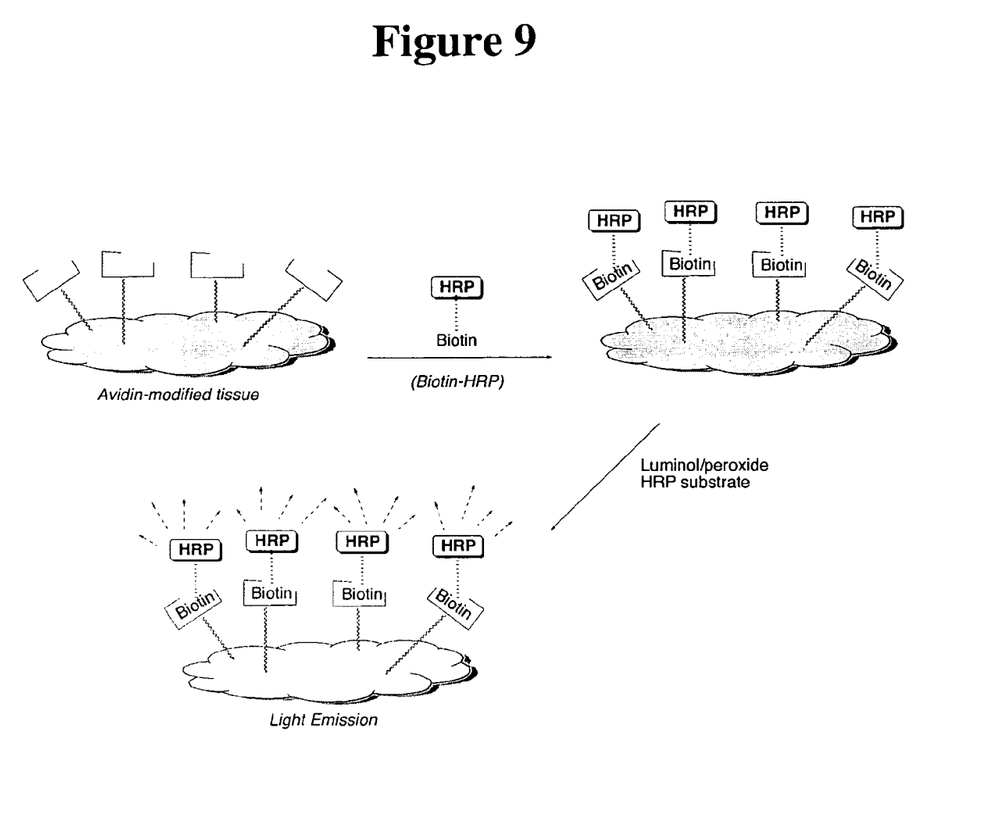
FIG. 9 shows a general scheme for detection of avidin-modified tissue by chemiluminescence.

Tissue that has been directly modified with avidin (via reduction followed by alkylation with avidin maleimide) can also be detected using chemiluminescence, as in the general scheme shown in FIG. 9. Other enzyme systems such as β-galactosidase and X-Gal (which results in a visual blue precipitate) can also be used but with lower sensitivity.

For the following examples, fresh animal parts were purchased from H&B Packing Co. (Waco, Tex.—bovine menisci) or Animal Technologies, Inc. (Tyler, Tex.—all other tissues). Tissue samples were used fresh (within one week of harvest), stored at 4° C., and kept hydrated by continuous exposure to a PBS solution. Meniscal and corneal tissues were dissected to afford thin and relatively flat sections. Skin and pericardium were cleaned to remove fat and connective tissue. Chemical reagents were the best grade available and were purchased from VWR (Poole, England), Pierce (Rockford, Ill.), Sigma-Aldrich (St. Louis, Mo.), or Molecular Probes (Eugene, Oreg.). Images were acquired on a Fluor-S Multi-Imager (Bio-Rad Laboratories, Inc., Hercules, Calif.) and analyzed using the Bio-Rad software.

EXAMPLE 1

Direct Alkylation with Spatial Resolution

A sample of fresh bovine pericardium was cleared of fat and cut to fit on a 96-well plate. 210 μL of a 0.1 M solution of NHS-LC-biotin (the N-hydroxysuccinimide ester of the 6-aminohexanoic acid amide of biotin) in PBS (10% v/v DMSO added for solubility) was added to wells to be modified, and 210 μL PBS (also 10% DMSO) was added to all other wells to serve as a control. The tissue sample was placed over the filled wells, a solid glass cover was clamped into place using spring clamps, and the entire apparatus was flipped over so that the reagents contacted the tissue surface. After the tissue had been exposed for about 12 hours at room temperature, the apparatus was dissembled and the tissue was transferred to a small Petri dish and thoroughly washed with PBS three times for ten minutes with a change of solution between each wash.

The final wash solution was replaced by a PBS solution of avidin-horseradish peroxidase (0.03 mg/ml) and the tissue was incubated for 2 hours at room temperature. The tissue samples were once again washed with PBS three times for ten minutes with a change of solution between each wash and then immersed in the chemiluminescence substrate (Supersignal® West Pico, Pierce) at room temperature for 3-5 minutes. The tissue was then removed from the luminal solution, blotted with paper towels to remove excess solution, placed on a sheet of plastic film, and placed into the imager for detection of the chemiluminescence using ultrasensitive chemiluminescence settings with the aperture completely open and 100 second acquisition.

The positive signal appeared as a series of bright dots corresponding to regions of the tissue which had been contacted with the wells containing NHS-LC-biotin.

EXAMPLE 2

Oxidation and Alkylation of Tissue Segments

A sample of fetal pig skin was cleared of fat and cut into squares approximately 1 cm/side. Skin samples were placed into the compartments of a 12 well plate and approximately 1.5 mL of a 0.08 M solution of sodium periodate in PBS was added to half of the wells. Additional wells were filled with 1.5 mL of PBS to serve as control samples. The samples were incubated for 8 hours at room temperature and then the solutions were decanted and the tissue samples washed thoroughly with PBS three times for ten minutes with a change of solution between each wash.

After washing all of the tissue samples were incubated in a PBS solution of biotin-hydrazide (with 10% v/v DMSO to assist in solubilizing the reagent) overnight (approximately 15 hours) at 4° C. The tissue was then thoroughly washed with PBS three times for ten minutes with a change of solution between each wash, and the final wash solution was replaced by a PBS solution of avidin-horseradish peroxidase (0.03 mg/ml). After incubation for 2 hours at room temperature the tissue samples were once again washed with PBS three times for ten minutes with a change of solution between each wash and then immersed in the chemiluminescence substrate (Supersignal® West Pico, Pierce) at room temperature for 3-5 minutes. The tissue was then removed from the luminal solution, blotted with paper towels to remove excess solution, placed on a sheet of plastic film, and placed into the imager for detection of the chemiluminescence using ultrasensitive chemiluminescence settings with the aperture completely open and 100 second acquisition.

The positive signal appeared as a relatively bright, uniform tissue sample for those tissue samples which had been incubated with sodium periodate, while the control samples were dark and almost undetectable.

EXAMPLE 3

Reduction and Alkylation with Spatial Resolution

A sample of fresh bovine pericardium was cleared of fat and cut to fit on a 1536-well plate. 10 μL of a 0.1 M solution of TCEP in PBS was added to wells to be reduced, the tissue sample was placed over the plate, a solid glass cover was clamped into place using spring clamps, and the entire apparatus was flipped over so that the reagents contacted the tissue surface. After the tissue was exposed for 50 minutes at room temperature, the apparatus was dissembled and the tissue was transferred to a small Petri dish. The tissue was thoroughly washed with PBS three times for ten minutes, with a change of solution between each wash. After reduction, the pericardium tissue appeared significantly more translucent.

The PBS wash solution was then replaced by a solution of avidin-maleimide (0.20 mg/ml in PBS) and the tissue incubated overnight (approximately 15 hours) at 4° C. The tissue was then thoroughly washed with PBS three times for ten minutes with a change of solution between each wash, and the final wash solution replaced by a PBS solution of biotin-horseradish peroxidase (0.03 mg/ml). After incubation for 2 hours at room temperature the tissue was once again washed with PBS three times for ten minutes with a change of solution between each wash and then immersed in the chemiluminescence substrate (Supersignal® West Pico, Pierce) at room temperature for 3-5 minutes. The tissue was then removed from the luminal solution, blotted with paper towels to remove excess solution, placed on a sheet of plastic film, and placed into the imager for detection of the chemiluminescence using ultrasensitive chemiluminescence settings, with the aperture completely open, for 100 second acquisition.

The positive signal appeared as a series of bright dots corresponding to the regions where the wells containing TCEP had contacted the tissue.

EXAMPLE 4

Reduction and Alkylation with a Dose Response Determination

Figure 10:
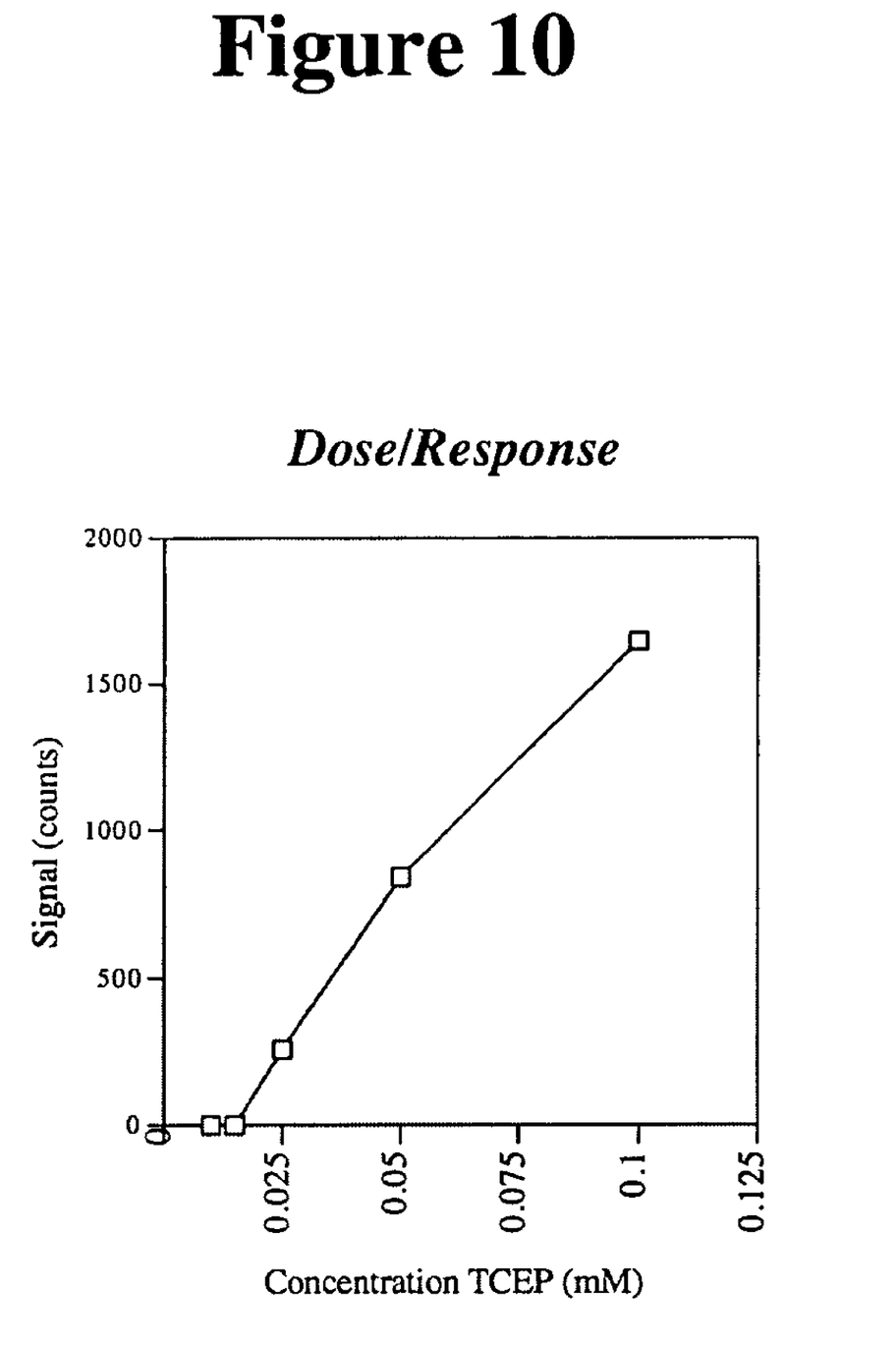
FIG. 10 shows the dose-response analysis of a tissue sample at various locations after undergoing TCEP reduction, followed by incubation with avidin-maleimide, biotin-HRP, and luminal.

A sample of fresh bovine pericardium was cleared of fat and cut to fit on a well plate. Various concentrations of TCEP in PBS were added to columns 1, 3, 5, 7, 9, and 11 of the plate at 210 µL solution per well (0.1, 0.05, 0.025, 0.015, 0.01, and 0.005 M TCEP, respectively). The wells in the control columns (2, 4, 6, and 8) contained PBS. The tissue sample was placed over the plate, and the remainder of the experiment proceeded as described in Example 3, including the tissue washes, alkylation with avidin-maleimide, further tissue washes, incubation with biotin-HRP, further tissue washes, and incubation with luminal. The positive signal appeared as a series of bright dots with the brightest dots appearing in the columns having the greatest concentration of TCEP. The relationship of signal to the concentration of reducing agent is clearly shown in FIG. 10. The signal is the average value (number of counts) for a given column as measured by the Bio-Rad software.

EXAMPLE 5

Reduction and Alkylation with Quantification

A sample of fetal pig skin (second trimester) was cleared of fat and connective tissue and cut to fit on a well plate. 10 µL of a 0.1 M solution of TCEP in PBS was added to wells to be reduced, the tissue sample was placed over the plate, a solid glass cover was clamped into place using spring clamps, and the entire apparatus was flipped over so that the reagents contacted the tissue surface. After the tissue had been exposed for 50 minutes at room temperature, the apparatus was dissembled and the tissue was transferred to a small Petri dish and thoroughly washed with PBS three times for ten minutes with a change of solution between each wash. The PBS wash solution was then replaced by a solution of avidin-maleimide (0.25 mg/ml in PBS) and the tissue incubated overnight (approximately 15 hours) at 4° C. The tissue was then thoroughly washed with PBS three times for ten minutes with a change of solution between each wash.

At the same time, a slot blot was prepared with serial dilutions of avidin of 20, 10, 5, 2.5, 1.25, and 0.625 µg/mL blotted on the nitrocellulose membrane, corresponding to 4, 2, 1, 0.5, 0.25, and 0.125 µg per 200 µL applied to each slot. The membrane was placed into the Petri dish with the tissue sample and processed alongside it. The tissue and the nitrocellulose membrane were then immersed in a PBS solution of biotin-horseradish peroxidase (0.03 mg/ml) for 2 hours at room temperature, then washed with PBS three times for ten minutes with a change of solution between each wash, and finally immersed in the chemiluminescence substrate (Supersignal® West Pico, Pierce) at room temperature for 3-5 minutes. The tissue and membrane were then removed from the luminal solution, blotted with paper towels to remove excess solution, placed on a sheet of plastic film, and placed into the imager for detection of the chemiluminescence using ultrasensitive chemiluminescence settings with the aperture completely open for a 100 second acquisition. The positive signal appeared as a bright signal against a dark background.

Only the two highest concentrations of avidin on the slot blot were evident under these conditions. The strongest signal came from the application of 4 µg of avidin to the slot, which corresponds to about 1 µg/mm$^2$ if quantitative immobilization is assumed. Since the signal intensity on the tissue was approximately the same as the strongest signal from the slot blot (determined using freely available NIH ImageJ 1.32j imaging software), it was determined that the amount of protein immobilized on the tissue was at least 1 µg/mm$^2$.

What is claimed is:

1. A method for covalent modification of a fresh collagenous tissue surface using a modifying agent, comprising:
    exposing the fresh collagenous tissue surface without fixing the tissue to an oxidizing agent to give an oxidized tissue surface; and
    exposing the oxidized tissue surface to the modifying agent, wherein the modifying agent is a nucleophilic reagent which undergoes condensation with the tissue surface.
2. The method of claim 1, wherein the oxidizing agent is sodium periodate.
3. The method of claim 1, wherein the modifying agent is a hydrazide reagent.
4. The method of claim 1, wherein the modifying agent is biotin hydrazide.
5. The method of claim 1, wherein the collagenous tissue surface is exposed to the oxidizing agent in spatially localized regions.
6. A method for covalent modification of a fresh collagenous tissue surface with a modifying agent, comprising:
    exposing the fresh collagenous tissue surface without fixing the tissue to sodium periodate to give an oxidized tissue surface; and
    exposing the oxidized tissue surface to a hydrazide reagent or biotin hydrazide.

* * * * *